US009387462B2

(12) United States Patent
Partridge et al.

(10) Patent No.: US 9,387,462 B2
(45) Date of Patent: Jul. 12, 2016

(54) CATALYST AND METHOD OF CATALYST MANUFACTURE

(75) Inventors: Martin Graham Partridge, Great Gransden (GB); Marinus Johannes Vissenberg, Dinslaken (DE); Anders Gabrielsson, Yarm (GB)

(73) Assignee: Johnson Matthey PLC, London (GB)

( * ) Notice: Subject to any disclaimer, the term of this patent is extended or adjusted under 35 U.S.C. 154(b) by 776 days.

(21) Appl. No.: 13/520,430

(22) PCT Filed: Dec. 23, 2010

(86) PCT No.: PCT/GB2010/052203
§ 371 (c)(1),
(2), (4) Date: Dec. 4, 2012

(87) PCT Pub. No.: WO2011/080515
PCT Pub. Date: Jul. 7, 2011

(65) Prior Publication Data
US 2013/0079568 A1   Mar. 28, 2013

(30) Foreign Application Priority Data

Jan. 4, 2010   (GB) .................................. 1000045.3

(51) Int. Cl.
*B01J 23/755* (2006.01)
*B01J 37/08* (2006.01)
(Continued)

(52) U.S. Cl.
CPC ............... *B01J 23/755* (2013.01); *B01J 21/04* (2013.01); *B01J 23/72* (2013.01); *B01J 23/75* (2013.01); *B01J 35/0026* (2013.01); *B01J 35/0053* (2013.01); *B01J 35/0073* (2013.01); *B01J 35/023* (2013.01); *B01J 35/109* (2013.01); *B01J 35/1047* (2013.01); *B01J 37/0203* (2013.01); *B01J 37/024* (2013.01);
(Continued)

(58) Field of Classification Search
None
See application file for complete search history.

(56) References Cited

U.S. PATENT DOCUMENTS 4,435,278 A  *  3/1984  Chen .......................... 208/251 H
4,490,480 A     12/1984  Lok et al.
(Continued)

FOREIGN PATENT DOCUMENTS

CN    1249208 A    4/2000
CN    1293594 A    5/2001
(Continued)

OTHER PUBLICATIONS

International Search Report dated Dec. 2013, from Chinese Application No. 201080063876.0.
(Continued)

*Primary Examiner* — Colin W Slifka
(74) *Attorney, Agent, or Firm* — RatnerPrestia

(57) ABSTRACT

The catalyst of the invention is a particulate catalyst in the form of particles having a minimum dimension of at least 0.8 mm, including a transition metal or a compound thereof dispersed on a porous support material, characterized in that said catalyst particles comprise at least 35% w/w total transition metal; and the transition metal surface area of said catalyst is at least 110 m² per gram of transition metal and the tapped bulk density of a bed of the catalyst particles is at least 0.7 g/ml. The method of making a catalyst includes multiple steps of impregnation of a porous support with a metal ammine solution followed by drying, calcination and reduction of the dried material. The catalyst is useful in hydrogenation reactions.

14 Claims, 1 Drawing Sheet

(51) Int. Cl.
  *C07C 5/02* (2006.01)
  *B01J 21/04* (2006.01)
  *B01J 23/72* (2006.01)
  *B01J 23/75* (2006.01)
  *B01J 35/00* (2006.01)
  *B01J 35/02* (2006.01)
  *B01J 35/10* (2006.01)
  *B01J 37/02* (2006.01)
  *B01J 37/18* (2006.01)

(52) U.S. Cl.
  CPC ............ *B01J 37/0205* (2013.01); *B01J 37/08* (2013.01); *B01J 37/18* (2013.01); *C07C 5/02* (2013.01)

(56) References Cited

U.S. PATENT DOCUMENTS

| | | | |
|---|---|---|---|
| 4,863,894 A | | 9/1989 | Chinchen et al. |
| 4,920,089 A | | 4/1990 | Van Beek et al. |
| 5,360,777 A | * | 11/1994 | Davis et al. .................. 502/202 |
| 5,906,731 A | * | 5/1999 | Abdo et al. ................ 208/216 R |
| 6,043,187 A | | 3/2000 | Harle et al. |
| 6,448,457 B1 | | 9/2002 | Hesse et al. |
| 7,560,413 B2 | | 7/2009 | Lok |
| 2002/0016519 A1 | | 2/2002 | Lok |
| 2003/0119668 A1 | | 6/2003 | Lok et al. |

FOREIGN PATENT DOCUMENTS

| | | |
|---|---|---|
| EA | 005420 B1 | 2/2005 |
| EP | 0 202 824 A2 | 11/1986 |
| JP | 57-12832 | 1/1982 |
| JP | 58-193734 | 11/1983 |
| JP | 64-47447 | 2/1989 |
| JP | 2002-505312 | 2/2002 |
| JP | 2002-510544 | 4/2002 |
| RU | 2 235 587 C2 | 9/2004 |
| WO | WO-99/51340 A1 | 10/1999 |
| WO | WO-2010/128137 A2 | 11/2010 |

OTHER PUBLICATIONS

Japanese Office Action for Patent Application No. 2012-546504 dated Apr. 1, 2014.
Evans et al., "On the Determination of Copper Surface Area by Reaction with Nitrous Oxide," *Applied Catalysis*, 1983, vol. 7, pp. 75-83.
International Search Report dated Jul. 7, 2011, from PCT International Application No. PCT/GB2010/052203.
International Preliminary Report on Patentability dated Jul. 4, 2012, from PCT International Application No. PCT/GB2010/052203.

* cited by examiner

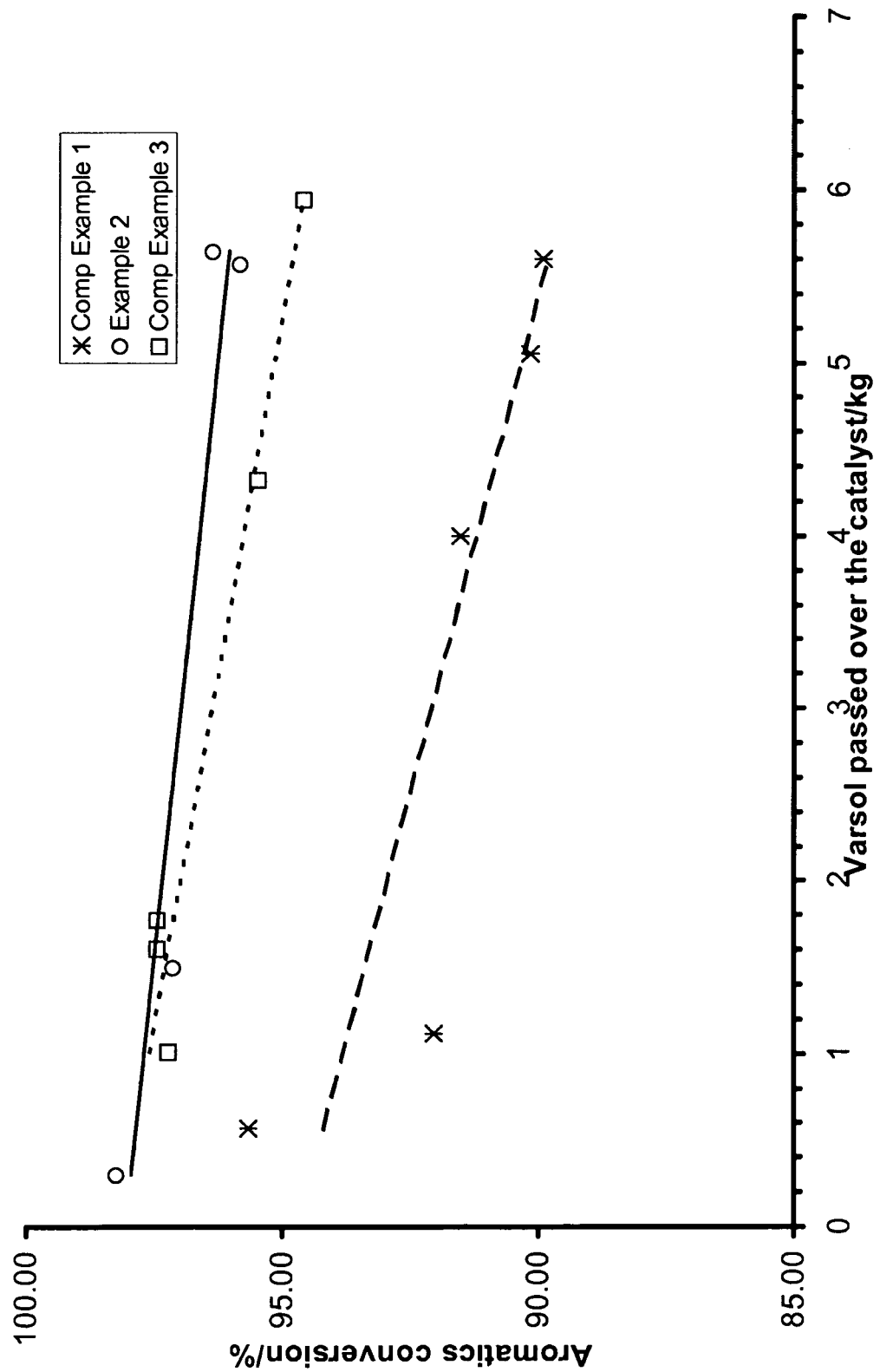

CATALYST AND METHOD OF CATALYST MANUFACTURE

CROSS-REFERENCE TO RELATED APPLICATIONS

This application is the U.S. National Phase application of PCT International Application No. PCT/GB2010/052203, filed Dec. 23, 2010, and claims priority of British Patent Application No. 1000045.3, filed Jan. 4, 2010, the disclosures of both of which are incorporated herein by reference in their entireties for all purposes.

FIELD OF THE INVENTION

The present invention relates to catalysts comprising one or more transition metals dispersed on a porous support.

BACKGROUND OF THE INVENTION

Catalysts comprising metals and metal compounds dispersed on a porous support material have been well known and used in the chemicals industry for many years, for a variety of purposes including hydrogenation, dehydrogenation of chemical feedstocks. U.S. Pat. No. 4,490,480 describes such catalysts, useful for various hydrogenation reactions, which consist of 5 to 40% (w/w) of nickel upon a transition alumina, in particular gamma alumina support. These catalysts have an active nickel surface area of between 80 and 300, preferably 100-250 $m^2/g$ of nickel and the nickel crystallites have an average diameter of 1 to 5, preferably 1.5 to 3 nm. The nickel crystallites are dispersed for at least 95% in the pores of the alumina. The patent describes a method of making catalysts by heating an aqueous suspension or mixture of a transition alumina in a dissolved nickel ammine complex for some time to a temperature of 60-100° C., preferably 75-95° C., which causes the precipitation of nickel hydroxide. The catalyst suspension is separated off and, if desired, washed, thereafter dried and calcined to nickel oxide and, if need be, reduced. Alternatively, alumina pellets or extrudates are impregnated with a concentrated solution of a nickel ammine complex; subsequently nickel is precipitated by temperature increase.

U.S. Pat. No. 4,920,089 provides a nickel upon transition alumina catalyst containing 5-40% w/w of nickel, with an active nickel surface area between 80 and 300 $m^2/g$ of Ni, with a transition alumina that satisfies a particular X-ray diffraction pattern. Preferably, the BET total surface area of the catalyst is between 50 and 200 $m^2/g$ catalyst and is substantially free from pores with a radius below 2.0 nm. The catalysts were prepared by impregnating shaped theta-alumina particles with an ammoniacal nickel solution having a particularly high pH value, namely between 9 and 11, and subsequently evaporating the impregnated alumina particles to dryness, calcining and reducing.

The methods described in the above-mentioned prior art patents enable highly disperse and active metal catalysts to be formed which have been highly successful. We have found, however, that it has not been possible to prepare catalysts in the form of pellets or shaped forms suitable for fixed bed-type reactions which have a metal content greater than about 33% w/w and which have a high metal dispersion coupled with a high crush strength. It is an object of the invention to provide such a catalyst.

SUMMARY OF THE INVENTION

According to the invention we provide a particulate catalyst in the form of particles having a minimum dimension of at least 0.8 mm, comprising a transition metal or a compound thereof dispersed on a porous support material, characterised in that said catalyst particles comprise at least 35% w/w total transition metal; and the transition metal surface area of said catalyst is at least 110 $m^2$ per gram of transition metal and the tapped bulk density of a bed of the catalyst particles is at least 0.7 g/ml.

According to a second aspect of the invention, we provide a method for making a catalyst comprising a transition metal or a compound thereof dispersed on a porous support material, said catalyst containing at least 35% w/w of total transition metal, comprising the steps of:
a) providing a solution of an ammine complex of said transition metal;
b) impregnating a porous support material in the form of particles having a minimum dimension of at least 0.5 mm and wherein the total pore volume is greater than 1.0 ml/g with said solution of ammine complex;
c) drying the impregnated support particles resulting from step (b);
d) repeating steps (b) and (c) at least four more times until the amount of transition metal in the particle is of the required level, and including a step of
e) calcining the dried impregnated support particles from step (c) at a temperature and duration sufficient to convert at least a majority of the transition metal compounds in the support to transition metal oxides;
f) optionally reducing at least 50% of the remaining transition metal compound and transition metal oxide to elemental metal.

The transition metal is preferably selected from cobalt, nickel or copper and may comprise more than one transition metal.

BRIEF DESCRIPTION OF THE DRAWING

The invention is further described by reference to the following FIGURES in which:

FIG. 1 is a plot of conversion vs. feed processed using the catalysts of Comparative Example 1, Example 2, and Comparative Example 3.

DETAILED DESCRIPTION OF THE INVENTION

The catalysts of the invention are particularly useful in hydrogenation reactions, i.e. for hydrogenating hydrogenatable organic compounds including unsaturation in olefinic or aromatic compounds and functional groups including carbonyl compounds, nitro-groups, nitriles and hydrogenolysis of esters. The catalysts may be particularly useful in the dearomatisation of solvents, for example.

The total transition metal in the particulate catalyst is at least 35% w/w. Total transition metal means the mass of metal whether present as elemental reduced metal or as a metal compound, expressed as a percentage of the total catalyst mass. The amount of metal may be measured by X-ray fluorescence (XRF) or inductively coupled plasma atomic emission spectrometry (ICP-AES). For the purposes of determining the total metal content of the catalysts described and claimed herein, we use ICP-AES, using a copper sulphate internal standard and calibrated using standard nickel sulphate solutions. Both methods are well known for use in determining metal content of materials such as catalysts and the skilled person will have such methods available to him.

The tapped bulk density of the catalyst is at least 0.7 g/ml when measured using the following method. A 100 g (approximately) sample of catalyst particles is accurately weighed into a standard 250 ml measuring cylinder, placed on the platform of an automated tapped bulk density analyser and tapped 2000 times before measuring the volume of the sample. The bulk density is then calculated as the accurate weight of the catalyst in grams divided by the volume of the sample after tapping. The bulk densities recorded in this document are measured using a Quantachrome Dual Autotap™ instrument, available from Quantachrome Instruments. Preferably the tapped bulk density of the catalyst particles is at least 0.75 g/ml.

Although catalysts containing 35% of nickel and having relatively high nickel metal surface areas are known in the form of powders and fine particles, we believe that such catalysts in the form of particles having a minimum dimension of at least 0.8 mm and a tapped bulk density of at least 0.7 are new. Particles having a minimum dimension of at least 0.8 mm include formed catalyst shapes such as spheres, cylinders, lobed cylinders (i.e. shapes having a transverse cross-section in the shape of a multi-lobed circle such as trilobes, quadrolobes or pentalobes), wheels, rings, saddles and other known shapes. Some shapes may include channels, recesses or holes. The minimum dimension may be the diameter or length as appropriate. Preferably the minimum dimension is at least 1 mm. Normally the catalyst particles are measured and an average minimum dimension is established. The minimum dimension FIGURES used in this document is calculated as an average of the measured minimum dimension of 40 catalyst particles.

The particles may be formed by granulation, tabletting, extrusion or other known methods. Extruded particles are preferred. In a preferred embodiment of the invention the catalyst particles comprise extruded cylinders or lobed cylinders. Such particles are suitable for use in fixed bed reactors, wherein a feed compound or mixture of compounds is caused to flow over and/or through a bed of catalyst particles. For use in a catalyst bed it is necessary that the catalyst particles are sufficiently strong to remain intact within the bed. Preferably the catalyst particles have a crush strength of at least 10 N/mm, more preferably at least 12 N/mm, expressed as the average crush strength of 25 particles. The crush strength of 25 particles is measured using an Engineering Systems CT5, ½ tonne crush test machine. The average crush strength per unit length is then calculated from the average force divided by the average length of the particles. The particles are heated to 500° C. in a nickel crucible for one hour prior to testing and then maintained at 100° C. to avoid absorption of moisture.

The porous support material is preferably a transition alumina. The transition alumina may include delta, eta, gamma and/or theta aluminas. One preferred embodiment uses a transition alumina comprising mainly gamma-phase alumina. The support material is generally in the form of shaped, e.g. extruded, particles as described above for the catalyst. The porous support material preferably has a total pore volume, as measured by mercury intrusion, of at least 1.0 ml/g. The porous support material preferably has a total surface area, as measured by BET methods, of at least 250 $m^2$/g. A particularly preferred porous support material is a transition alumina support having a pore volume of at least 1.0 ml/g and a bimodal pore size distribution. We have found that using a catalyst support of this type, it is possible to introduce a greater amount of the transition metal into the support material than in a support having a unimodal pore size distribution, while retaining sufficient crush strength for the catalyst to be used in a fixed bed. A preferred catalyst support has a pore size distribution, as measured by mercury porosimetry, in which at least 20% (more preferably at least 25%) of the total pore volume is contained in pores having a diameter of from 100 nm-700 nm and at least 30%, more preferably at least 40%, of the total pore volume is contained in pores having a diameter of from 5 nm-20 nm.

A transition metal ammine complex for use in preparing the catalysts according to the method of the invention may be made by dissolving a transition metal compound or a quantity of the transition metal in metallic form, in a solution of an ammonium compound, such as ammonium carbonate, in ammonium hydroxide. Transition metal ammine carbonate complexes are preferred but other anions may be used, such as sulphates, acetates or formates.

A cobalt ammine complex is most preferably a cobalt ammine carbonate complex which is formed in situ in aqueous solution by dissolving basic cobalt carbonate in a solution of ammonium carbonate in aqueous ammonium hydroxide, to give a product of the desired cobalt content. Alternatively other cobalt salts may be used, including organic salts such as cobalt acetate or cobalt formate. Nickel and copper ammine carbonate solutions may be prepared in a similar manner.

A cobalt ammine carbonate complex is the product of dissolving basic cobalt carbonate, preferably of empirical formula $Co(OH)_{2-2x}(CO_3)_x$, wherein $0 \le x \le 1$, in a solution of ammonium carbonate in aqueous ammonium hydroxide, to give a product of the desired cobalt content. The cobalt ammine carbonate solution may be made by dissolving basic cobalt carbonate in an aqueous solution of ammonium carbonate or ammonium carbamate containing additional ammonium hydroxide. The relative amounts should be such that the pH of the solution is in the range 7.5 to 12, preferably 9 to 12. The solution preferably contains 0.1 to 2.5 moles of the cobalt complex per liter. As the concentration of cobalt increases, then generally the proportion of carbonate ions relative to hydroxide ions in the basic cobalt carbonate feed should be increased. Additional ammonium hydroxide solution may be added if required to reduce the viscosity of the solution. As an alternative, the cobalt ammine carbonate solution may be made by dissolving metallic cobalt, preferably in powdered form, in aqueous ammonia of pH 11-12, in the presence of oxygen or air, either with addition of ammonium carbonate or with addition of $CO_2$ gas. A cobalt ammine complex solution may be allowed to oxidise before being impregnated into the catalyst support, either by aging in contact with an oxygen-rich gas or by chemical or electrochemical oxidation in order that the Co(II) complex is converted, at least in part, to a Co(III) complex.

When the transition metal is nickel, the catalysts may be made by impregnating the porous support with the appropriate amount of an aqueous solution of a nickel ammine complex. A nickel ammine carbonate complex may be made by dissolving basic nickel carbonate in a solution of ammonium carbonate in aqueous ammonium hydroxide, to give a product of the desired nickel content. The solution of the nickel ammine complex preferably has a pH in the range 9 to 10.5.

A copper ammine carbonate solution may be made by dissolving basic copper carbonate in an aqueous solution of ammonium carbonate containing additional ammonium hydroxide. The relative amounts should be such that the pH of the solution is in the range 7-12, preferably 8-11. The solution preferably contains 2-5, particularly 2-4, moles of the copper complex per liter. As the concentration of copper increases, then generally the proportion of carbonate ions relative to hydroxide ions in the basic copper carbonate feed should be increased.

Preferably, the total number of impregnation steps (b) is at least five, more preferably at least six and the impregnated catalyst resulting from each step (b) is then dried in step (c). In a preferred method, steps (b) and (c) are carried out three times and then step (e) is carried out and then steps (b) and (c) are carried out at least once more (more preferably at least twice more, especially three times more) and then calcination step (e) is carried out a second time. Preferably, substantially all the transition metal compounds are converted to transition metal oxides in step (e).

Preferably, the calcined catalyst from the final calcination step (e) is reduced in a hydrogen-containing gas. Preferably the reduced catalyst is then passivated using an oxygen containing gas, using conventional catalyst passivation methods, such that the catalyst temperature does not exceed 100° C. when exposed to air. Proper passivation of the catalyst allows it to be stored and handled in air without catching fire due to the pyrophoric nature of finely divided metal particles, as is well known.

The dried impregnated support particles are calcined according to step (e) of the method, preferably following at least every three impregnation and drying steps. Preferably a calcination step is carried out when the amount of transition metal in the particle has, by means of sufficient successive impregnation steps, reached the required level.

The transition metal surface area of the catalyst is at least 110 m² per gram of transition metal. The surface area of the transition metal is measured following reduction of the metal to its elemental state. When the transition metal is nickel, the nickel metal surface area is at least 110 m² per gram of total nickel present in the catalyst as measured by hydrogen chemisorption after the catalyst has been reduced in flowing hydrogen at a pre-determined reduction temperature for one hour. The reduction step is a part of the surface area measurement procedure and is done in order to reduce the nickel compounds to elemental nickel for measurement of hydrogen chemisorption.

When the nickel in the catalyst is substantially or wholly in the form of oxidic nickel compounds, the pre-determined reduction temperature is 430° C. When the nickel in the catalyst is largely or substantially in elemental form, i.e. when the catalyst has been pre-reduced and passivated then the pre-determined reduction temperature is 240° C. 0.7-0.8 g of sample is accurately weighed and transferred to the sample cell of a chemisorption apparatus. The hydrogen flow through the sample cell is set to 250 cm³ min⁻¹. The temperature is then raised at a ramp rate of 3° C. min⁻¹ to the selected reduction temperature and held constant for one hour. Following reduction the H₂ flow is stopped and the sample cell is outgassed at 450° C. under vacuum for six hours, and then allowed to cool to 50° C. while maintaining the vacuum. Chemisorption of H₂ is carried out over a range of pressures between 100 and 760 torr. The sample is allowed to equilibrate at each pressure for 60 seconds at each pressure. The volume of hydrogen chemisorbed at each pressure is plotted against pressure. The best linear portion of the isotherm is chosen and extrapolated back to zero pressure intercept to determine the monolayer capacity. The monolayer amount is the capacity divided by the sample weight in grams.

The specific nickel surface area is determined from the following equation:

$$S_{Ni} = [Nm \times NA \times S]/D$$

Where: $S_{Ni}$=specific nickel surface area, m²g-1
Nm=monolayer amount, mol g⁻¹
NA=Avogadro constant, $6 \times 10^{23}$ mol⁻¹
S=stoichiometry of H₂ adsorption which is taken to be 2
D=surface density of Nickel atoms, $1.54 \times 10^{19}$ atoms m².
Preferably the nickel metal surface area is at least 120 m²/g.

The cobalt surface area is determined by H₂ chemisorption. This method is used when a cobalt surface area measurement is mentioned in this specification for the catalysts of the invention containing cobalt as the transition metal (unless otherwise specified). Approximately 0.2 to 0.5 g of sample material is firstly degassed and dried by heating to 140° C. at 10° C./min in flowing helium and maintaining at 140° C. for 60 minutes. The degassed and dried sample is then reduced by heating it from 140° C. to 425° C. at a rate of 3° C./min under a 50 ml/min flow of hydrogen and then maintaining the hydrogen flow at 425° C. for 6 hours. Following this reduction, the sample is heated under vacuum to 450° C. at 10° C./min and held under these conditions for 2 hours. The sample is then cooled to 150° C. and maintained for a further 30 minutes under vacuum. The chemisorption analysis is then carried out at 150° C. using pure hydrogen gas. An automatic analysis program is used to measure a full isotherm over the range 100 mm Hg up to 760 mm Hg pressure of hydrogen. The analysis is carried out twice; the first measures the "total" hydrogen uptake (i.e. includes chemisorbed hydrogen and physisorbed hydrogen) and immediately following the first analysis the sample is put under vacuum (<5 mm Hg) for 30 minutes. The analysis is then repeated to measure the physisorbed uptake. A linear regression is then applied to the "total" uptake data with extrapolation back to zero pressure to calculate the volume of gas chemisorbed (V).

Cobalt surface areas are calculated in all cases using the following equation;

$$\text{Co surface area} = (6.023 \times 10^{23} \times V \times SF \times A)/22414$$

where
V=uptake of H₂ in ml/g
SF=Stoichiometry factor (assumed 2 for H₂ chemisorption on Co)
A=area occupied by one atom of cobalt (assumed 0.0662 nm²)

This equation is described in the Operators Manual for the Micromeretics ASAP 2010 Chemi System V 2.01, Appendix C, Part No. 201-42808-01, October 1996.

The copper surface area is conveniently determined by the nitrous oxide decomposition method, for example as described by Evans et al in "Applied Catalysis", 7, (1983), pages 75-83-a particularly suitable technique is described in EP 0 202 824. The methods are based on the decomposition of a nitrous oxide molecule on a copper surface which is accompanied by the liberation of one nitrogen molecule. In the following equation, the subscript s indicates surface atoms.

$$N_2O \text{ (gas)} + 2 Cu_s \rightarrow N_2(\text{gas}) + (Cu\text{—}O\text{—}Cu)_s$$

Reduction of the samples is carried out prior to copper surface area determination by heating the sample at a rate of 200 K/h in a current of hydrogen diluted with argon (67% H₂/33% Ar by volume) to a temperature of 393 K (120° C.) maintaining at this temperature for 30 min, then increasing the temperature at a rate of 100 K/h to the desired reduction temperature, and maintaining at that desired temperature for 1 h. After reduction, the sample is cooled to 90° C. at which temperature the nitrous oxide decomposition is effected using a mixture of nitrous oxide and argon (1% N₂O/99% Ar by volume). It is assumed that the adsorption stoichiometry of $Cu_s/O_{ads}$ was 2 and that the area occupied by one copper atom is 5.18 Å², i.e. at a 73% packing density, $1.46 \times 10^{19}$ surface copper atoms per m².

EXAMPLES

The invention is further illustrated by reference to the following Examples.

Comparative Example 1

250 g of ammonium carbonate was dissolved in 1 l of 33% aqueous ammonia solution by stirring for 3 hours. 350 g of basic nickel carbonate was then added to the ammonium carbonate solution in 50 g portions, stirring for 30 minutes after each addition. The resulting nickel hexammine solution is stored until required.

The support used was an extruded transition alumina (theta/delta) catalyst support, in the form of trilobes having a nominal diameter of 1.2 mm, average length of 2.9 mm and having a pore volume of 0.67 ml/g, a unimodal pore size distribution and a BET surface area of 110 m²/g. 100 g of the support was placed in a beaker and sufficient of the nickel hexamine solution was added to cover the catalyst pellets and to keep them covered during a soaking time of 2 minutes. The excess solution was then filtered off under water pressure and the wet pellets were dried at 150° C. in a rotary calcination tube for 30 minutes under flowing air. The nickel hexamine complex decomposes during this drying stage with the evolution of ammonia to produce "green" nickel hydroxycarbonate dispersed in the pores of the support. The impregnation and drying was repeated twice more and the product was then calcined in air at 280° C. for 45 minutes to convert the nickel hydroxycarbonate to nickel oxide. The catalyst was then reduced in flowing hydrogen while heating to 450° C. to achieve a final degree of reduction of at least 90%. Following reduction, the catalyst was passivated in a controlled nitrogen/oxygen mixture until stable in air. The nickel content was 21% and the Ni metal specific surface area was 140 m²/g. The tapped bulk density was 0.73.

Example 2

Preparation of Catalyst According to the Invention

A nickel hexamine carbonate solution was prepared as described in Comparative Example 1. the support used was a transition alumina 1.2 mm diameter extruded trilobe having a BET surface area of 265 m²/g. The pore volume was 1.1 ml/g and the pore size distribution was bimodal.

100 g of support was impregnated with nickel hexamine solution by soaking and drying three times followed by calcination as described for comparative Example 1. The resulting catalyst was then soaked a further three times, each soaking step being followed by a drying step as before. After the last drying step, the product was calcined, reduced, and passivated. The nickel content was found to be 39%, and the nickel metal specific surface area was 120 m²/g. The tapped bulk density was 0.86. The crush strength was 22 N/mm.

Comparative Example 3

A catalyst was prepared as described in Comparative Example 1, except that following the calcination step, the calcined material was impregnated and dried an additional three times. The material was then calcined once more and then reduced and passivated following the same procedure as described in Comparative Example 1. The total nickel content was 30.2% and the Ni metal specific surface area was 121 m²/g. The tapped bulk density was 0.89.

Catalyst Activity Test

The sample is tested as whole particles in a down-flow, fixed-bed reactor (22.22 mm I.D.). The catalyst is tested in the form of whole particles. The catalyst particles (50 cm³) are mixed with 24 g of silicon carbide to form a catalyst bed and the reactor also included a bed of silicon carbide at each end of the catalyst bed. The catalyst is activated by heating slowly at 1/minute in hydrogen flowing at 50 l/hr (1 BarG pressure) to 120° C., holding the temperature steady for one hour and than raising the temperature at 2°/minute to 230° C. then maintaining that temperature for one hour. The catalyst is then cooled to room temperature while maintaining the flow of hydrogen. The test was conducted at 30 BarG hydrogen pressure, 200° C. bed temperature and a LHSV of 4.5 h⁻¹. The feedstock used was Varsol™ 120 from Exxon, which is a naptha solvent, doped with benzothiophene to bring the S content to 24 ppm. The feed contained approximately 30% aromatics. The $H_2$/feed ratio used was 89. The test is run until 6 kg of feedstock have passed across the catalyst. The liquid product is sampled at intervals over the reaction time and analysed by multiwave UV for aromatics. The conversion (%) for each sample is obtained from the following:

Conversion (%)=[(AIN−AOUT)/AIN]×100

Where:
AIN=Aromatics In
AOUT=Aromatics Out

A plot of conversion against feed processed is constructed, using linear regression to obtain the best fit line. FIG. 1 shows the plots of results using the catalysts made in Comparative Example 1, Example 2 and Comparative Example 3. The graph shows that the catalyst of Example 2 has a higher activity throughout the duration of the test than the catalyst of Comparative Example 1 and maintains a high activity over a longer period than the catalyst of Comparative Example 3. The catalyst of Comparative Example 3 was made using the same method as the catalyst of Example 2, but the amount of nickel in the finished catalyst was considerably less. Without wishing to be bound by theory, we believe that the greater pore volume of the support used to make the catalyst of Example 2 allows more nickel to be absorbed into the pore structure of the catalyst support.

The invention claimed is:

1. A particulate catalyst in the form of particles having a minimum dimension of at least 0.8 mm, comprising a transition metal or a compound thereof dispersed on a porous support material, wherein said catalyst particles comprise at least 35% w/w total transition metal; and the transition metal surface area of said catalyst is at least 110 m² per gram of transition metal and the tapped bulk density of a bed of the catalyst particles is at least 0.7 g/ml,
wherein the porous support material has a bimodal port size distribution.

2. A catalyst according to claim 1, wherein the porous support comprises a transition alumina.

3. A catalyst according to claim 1, wherein the porous support material has a pore size distribution, as measured by mercury porosimetry, in which at least 20% of the total pore volume is contained in pores having a diameter of from 100 nm-700 nm and at least 30% of the total pore volume is contained in pores having a diameter of from 5 nm-20 nm.

4. A catalyst according to claim 1, wherein the porous support material has a pore volume of at least 1.0 ml/g.

5. A catalyst according to claim 1, wherein the porous support is in the form of extruded cylinders or lobed cylinders.

6. A catalyst according to claim 1, wherein the transition metal is selected from cobalt, nickel or copper and may comprise more than one transition metal.

7. A catalyst according to claim 1, wherein the transition metal comprises nickel.

8. A catalyst according to claim 1, wherein the metal surface area of said catalyst is at least 120 m² per gram of transition metal.

9. A method for making a particulate catalyst in the form of particles according to claim 1 comprising the steps of:
   a) providing a solution of an ammine complex of said transition metal
   b) impregnating a porous support material in the form of particles having a minimum dimension of at least 0.8 mm and wherein the total pore volume is greater than 1.0 ml/g with said solution of ammine complex;
   c) drying the impregnated support particles resulting from step (b)
   d) repeating steps (b) and (c) at least four more times until the amount of transition metal in the particle is of the required level, and including a step of
   e) calcining the dried impregnated support particles from step (c) at a temperature and duration sufficient to convert at least a majority of the transition metal compounds impregnated in the support to transition metal oxides;
   f) optionally reducing at least 50% of the remaining transition metal compound and transition metal oxide to elemental metal.

10. A method as claimed in claim 9, wherein said solution of an ammine complex is a nickel ammine carbonate solution.

11. A method as claimed in claim 9, wherein steps (b) and (c) are carried out three times and then step (e) is carried out and then steps (b) and (c) are carried out three times more and then step (e) is carried out a second time.

12. A method as claimed in claim 9, wherein the calcined catalyst from the final step (e) is reduced in a hydrogen-containing gas and then passivated using an oxygen containing gas such that the catalyst temperature does not exceed 100° C. when exposed to air.

13. A method of carrying out the hydrogenation of a hydrogenatable organic compound by contacting said hydrogenatable organic compound with a hydrogen-containing gas, characterised that said contact is carried out in the presence of a particulate catalyst made according to the method of claim 9.

14. A method of carrying out the hydrogenation of a hydrogenatable organic compound by contacting said hydrogenatable organic compound with a hydrogen-containing gas, characterised that said contact is carried out in the presence of a particulate catalyst according to claim 1.

\* \* \* \* \*